US009372138B2

(12) United States Patent  
Riddall

(10) Patent No.: US 9,372,138 B2  
(45) Date of Patent: Jun. 21, 2016

(54) CABLE TRACK MONITORING SYSTEM AND METHOD

(71) Applicant: HONDA MOTOR CO., LTD., Tokyo (JP)

(72) Inventor: Mike Riddall, Proton Station (CA)

(73) Assignee: Honda Motor Co., Ltd., Tokyo (JP)

( * ) Notice: Subject to any disclaimer, the term of this patent is extended or adjusted under 35 U.S.C. 154(b) by 168 days.

(21) Appl. No.: 14/185,297

(22) Filed: Feb. 20, 2014

(65) Prior Publication Data

US 2015/0122047 A1    May 7, 2015

(30) Foreign Application Priority Data

Nov. 5, 2013  (CA) .................................... 2832525

(51) Int. Cl.
  *G01N 3/08* (2006.01)
  *F16L 3/015* (2006.01)
  *G01L 5/10* (2006.01)
  *H02G 11/00* (2006.01)

(52) U.S. Cl.
  CPC . *G01N 3/08* (2013.01); *F16L 3/015* (2013.01); *G01L 5/103* (2013.01); *H02G 11/006* (2013.01)

(58) Field of Classification Search
  CPC ............. G01N 3/08; G01N 3/00; G01B 5/30; A62C 33/04
  USPC ................... 73/828, 826, 788, 796, 806, 760; 248/89
  See application file for complete search history.

(56) References Cited

U.S. PATENT DOCUMENTS

| | | | | |
|---|---|---|---|---|
| 3,779,003 A * | 12/1973 | Boissevain | ............. | F16G 13/16 248/49 |
| 4,426,875 A * | 1/1984 | Crosby, Jr. | ............... | G01N 3/08 73/12.13 |
| 5,918,288 A * | 6/1999 | Seppa | ..................... | G01L 5/103 73/862.391 |
| 6,205,867 B1 * | 3/2001 | Hayes | ..................... | G01C 9/00 73/862.391 |
| 6,978,595 B2 * | 12/2005 | Mendenhall | ............ | F16G 13/16 248/49 |
| 7,132,602 B1 * | 11/2006 | Komiya | ............... | H02G 11/006 174/70 R |
| 7,444,800 B2 * | 11/2008 | Hermey | ................. | F16G 13/16 248/49 |
| 7,513,096 B2 * | 4/2009 | Utaki | ..................... | F16G 13/16 248/49 |

(Continued)

FOREIGN PATENT DOCUMENTS

| KR | 100632083 B1 | 10/2006 |
|---|---|---|
| WO | 2011125046 A2 | 10/2011 |

OTHER PUBLICATIONS

Kabelschlepp, The QUANTUM Cable Carrier Series, 15 pp.
Xiao, et al., Research on Sag Online Monitoring System for Power Transmission Wire Based on Tilt Measurement, International Journal of Smart Grid and Clean Energy, vol. 2, No. 1, Jan. 2013.

*Primary Examiner* — Lisa Caputo
*Assistant Examiner* — Nigel Plumb
(74) *Attorney, Agent, or Firm* — Standley Law Group LLP

(57) ABSTRACT

Described are various exemplary embodiments of a cable track monitoring system and method. In one embodiment, a monitoring system for a cable track is operatively mounted between an anchoring unit and a mobile unit in designating a deployable cabling path therebetween as the mobile unit travels relative to the anchoring unit. The system comprises a monitoring cable to be run within the cable track along the cabling path; and a sensor fixedly mountable relative to one of the anchoring unit and the mobile unit and operatively coupleable to the monitoring cable in sensing a tension variation therein as the mobile unit travels relative to the anchoring unit. The sensor is operable to monitor the tension variation during operation of the cable track.

21 Claims, 4 Drawing Sheets

(56) References Cited

U.S. PATENT DOCUMENTS

| | | | | |
|---|---|---|---|---|
| 7,637,092 B2 * | 12/2009 | Utaki | ................... | F16G 13/16 248/49 |
| 7,786,894 B2 * | 8/2010 | Polk | ................... | H04L 12/66 324/764.01 |
| 8,155,921 B2 * | 4/2012 | O | ................... | H02G 1/02 702/166 |
| 8,550,236 B2 * | 10/2013 | Merten | ................... | B65G 23/44 198/502.1 |
| 2004/0103636 A1 * | 6/2004 | Komiya | ................... | F16G 13/16 59/78.1 |
| 2008/0189061 A1 * | 8/2008 | Scholtz | ................... | H02G 7/02 702/65 |
| 2009/0127527 A1 * | 5/2009 | Hoffend, III | ................... | A63J 1/028 254/338 |

\* cited by examiner

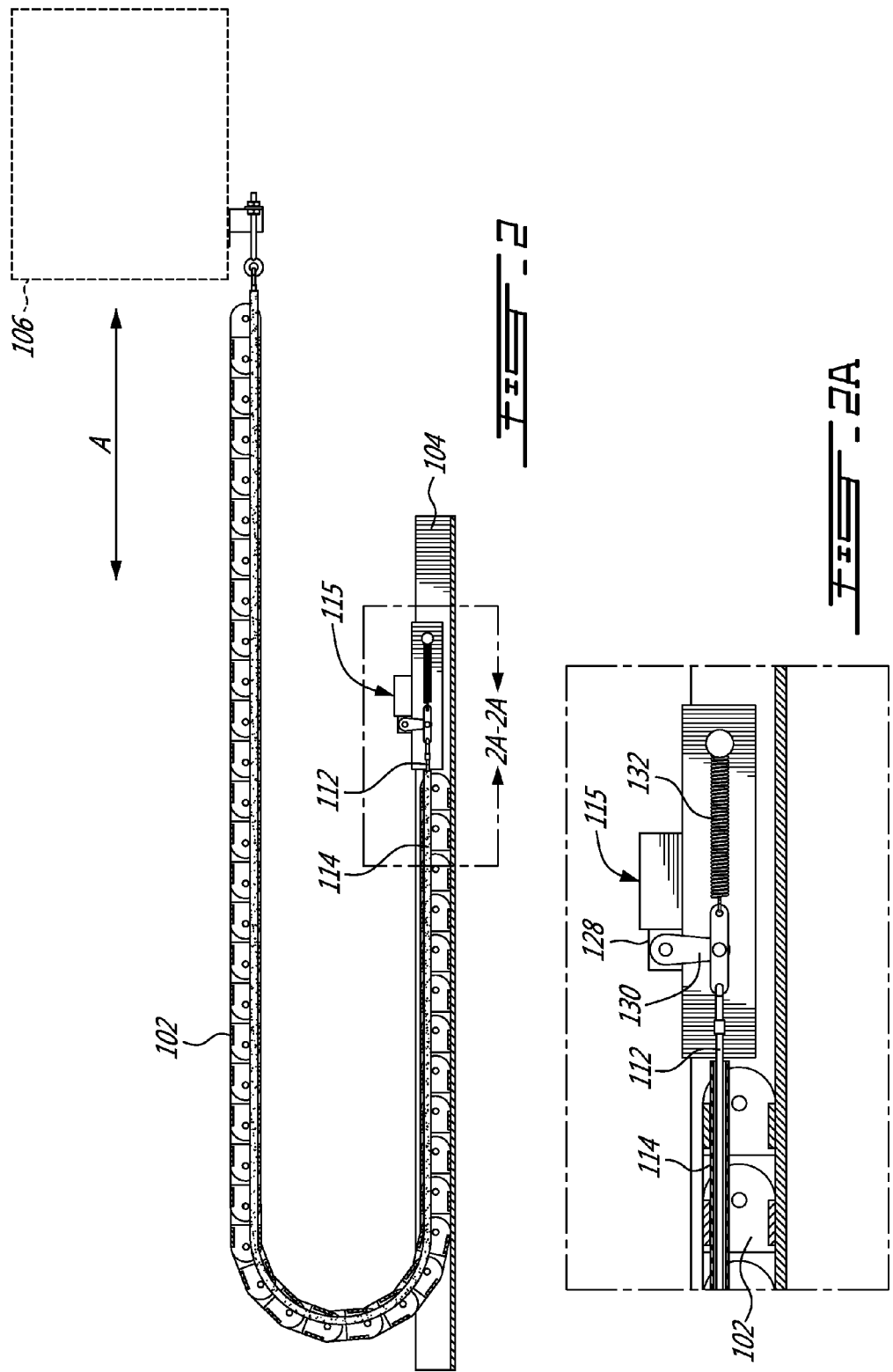

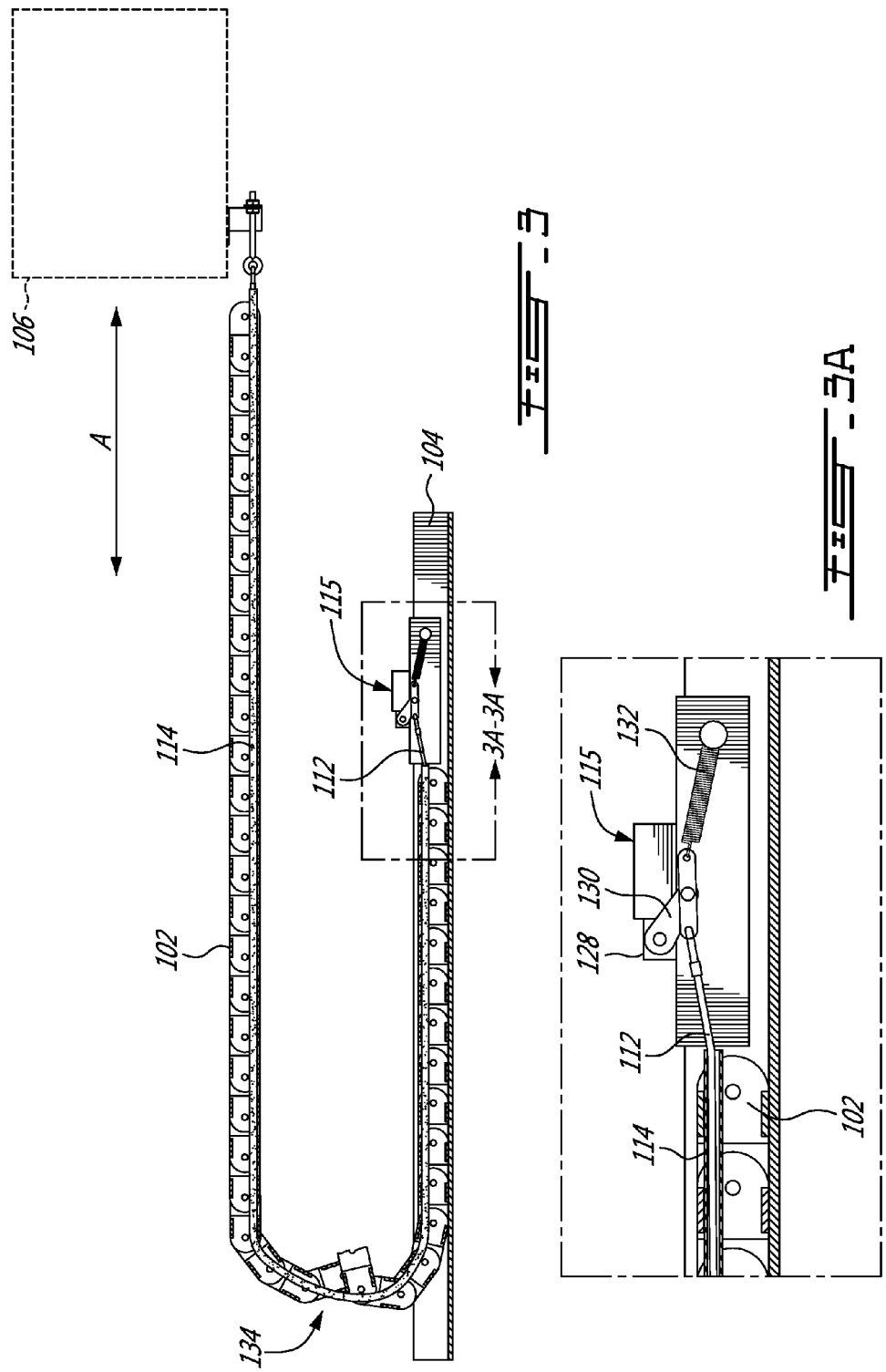

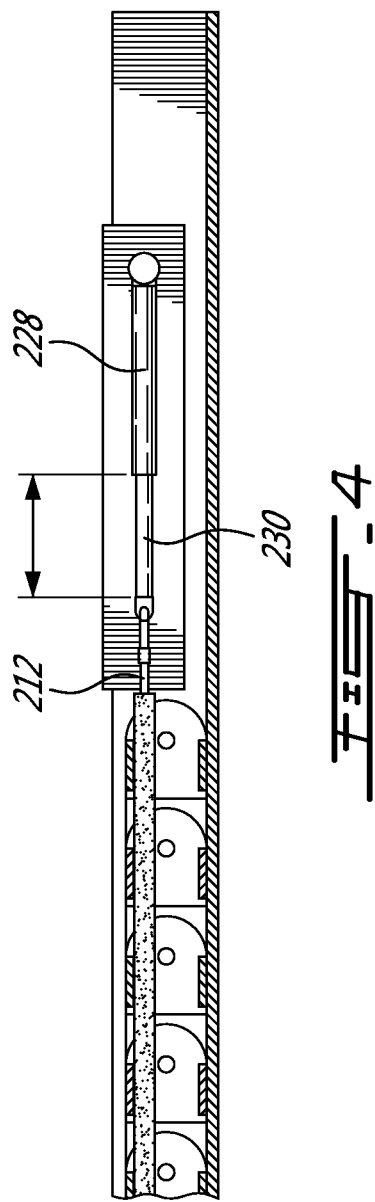
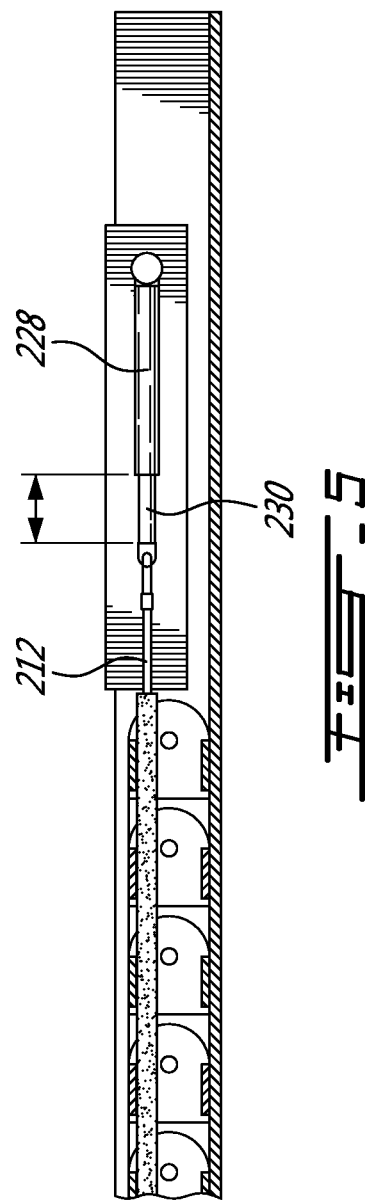

CABLE TRACK MONITORING SYSTEM AND METHOD

CROSS-REFERENCE TO RELATED APPLICATIONS

As authorized by 35 U.S.C. §119, this application claims priority to and hereby incorporates by reference Canadian Application Serial No. 2,832,525, titled CABLE TRACK MONITORING SYSTEM AND METHOD, filed Nov. 5, 2013.

FIELD OF THE DISCLOSURE

The present disclosure relates to cable tracks or carriers, and in particular, to a cable track monitoring system and method.

BACKGROUND

Cable tracks, also known as cable carriers, are known in the art to facilitate management of cables, wires and/or other conduits feeding a mobile station, for example in the context of an industrial assembly line or the like. For example, the cable track may house a number of cables or the like to guide them to a mobile device such that upon the mobile device travelling along a designated operational path, the cables are guided along that path to minimize cable obstructions, entanglements and/or other such undesirable cable management issues. In some examples, the mobile device travels along a vertical or horizontal path relative to a fixed cable anchoring or supply unit (e.g. cable outlet or the like). The cable track is then structurally coupled between the anchoring unit and the mobile unit so to form a designated path for the cables housed therein, which path is operatively defined by the furling and unfurling of the cable track as the mobile unit travels along the linear path.

This background information is provided to reveal information believed by the applicant to be of possible relevance. No admission is necessarily intended, nor should be construed, that any of the preceding information constitutes prior art.

SUMMARY

The following presents a simplified summary of the general inventive concept(s) described herein to provide a basic understanding of some aspects of the invention. This summary is not an extensive overview of the invention. It is not intended to restrict key or critical elements of the invention or to delineate the scope of the invention beyond that which is explicitly or implicitly described by the following description and claims.

There remains a need for a cable track monitoring system and method that overcome some of the drawbacks of known technologies, or at least, provides the public with a useful alternative. Some aspects of the below described embodiments provide such a system and method.

In accordance with one aspect, there is provided a monitoring system for a cable track operatively mounted between an anchoring unit and a mobile unit in designating a deployable cabling path therebetween as the mobile unit travels relative to the anchoring unit, the system comprising: a monitoring cable to be run within the cable track along the cabling path; and a sensor fixedly mountable relative to one of the anchoring unit and the mobile unit and operatively coupleable to said monitoring cable in sensing an undesirable tension variation therein as the mobile unit travels relative to the anchoring unit; wherein said sensor is operable produce an output indicative of said undesirable tension variation as representative of suboptimal operation of the cable track.

In accordance with another aspect, there is provided a method for monitoring a cable track operatively mounted between an anchoring unit and a mobile unit in designating a deployable cabling path as the mobile unit moves relative to the anchoring unit, the method comprising: running a monitoring cable along the cable track; monitoring tension variations in said monitoring cable as the mobile unit moves relative to the anchoring unit; and automatically producing an output signal representative of said monitored tension variations as indicative of a cable track operation.

Other aspects, features and/or advantages will become more apparent upon reading of the following non-restrictive description of specific embodiments thereof, given by way of example only with reference to the accompanying drawings.

BRIEF DESCRIPTION OF THE DRAWING FIGURES

Several exemplary embodiments of the present disclosure will be provided, by way of examples only, with reference to the appended drawings, wherein like reference numerals across the several views refer to identical or equivalent features, and wherein:

FIG. 2 is a cross sectional side view of the system of FIG. 1 showing a configuration of the monitoring system during normal operation of the cable track as the mobile unit is displaced horizontally relative to the anchoring unit;

FIG. 2A is an enlarged cross sectional view of a resiliently-biased sensing mechanism of the cable track monitoring system of FIG. 2 encased within line 2A-2A thereof;

FIG. 3 is a cross sectional side view of the system of FIG. 1 showing a configuration of the monitoring system during faulty operation of the cable track as the mobile unit is displaced horizontally relative to the anchoring unit;

Figure 1:
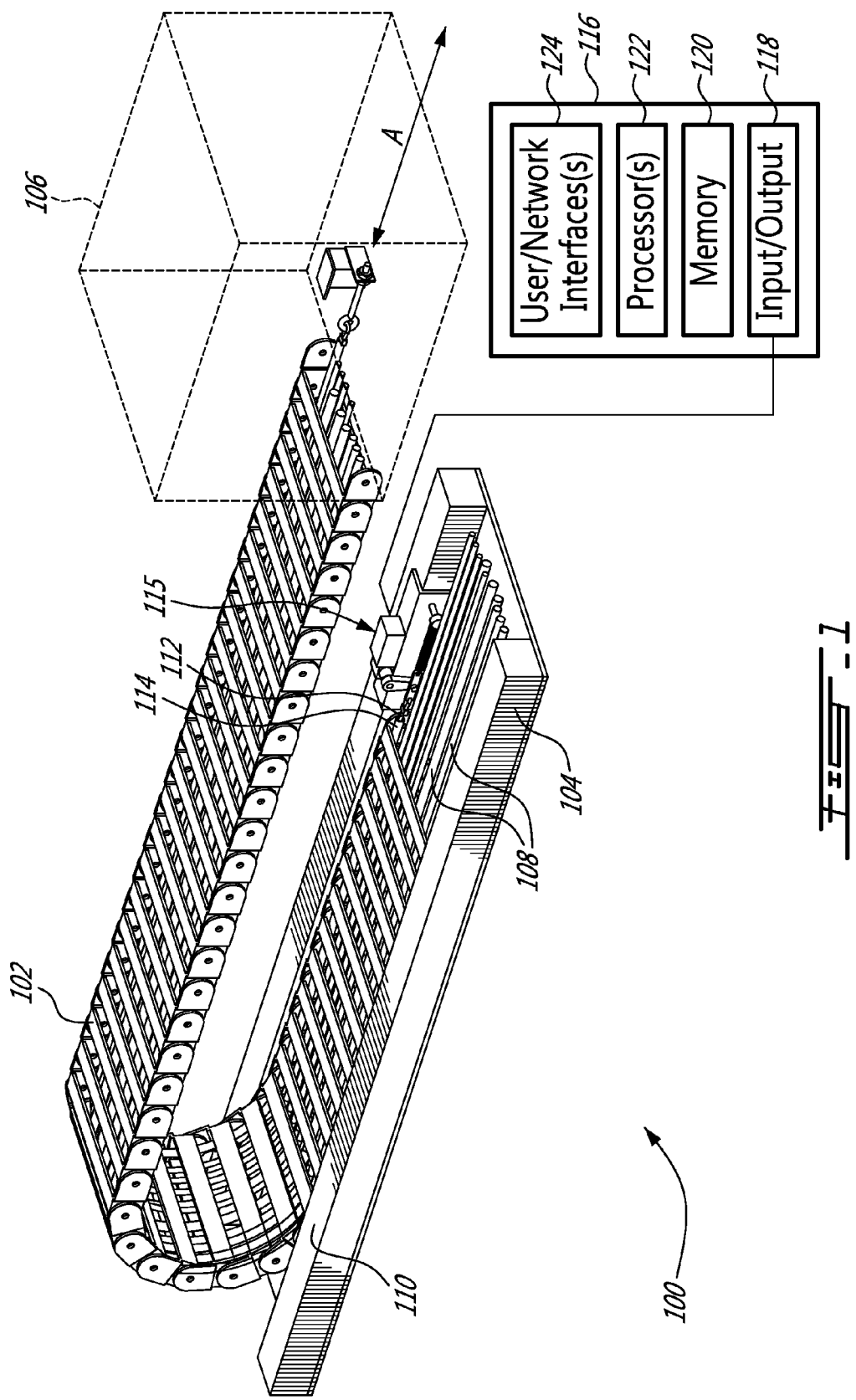
FIG. 1 is a perspective view of a cable track monitoring system operatively associated with an exemplary cable track mounted between a mobile unit and an anchoring unit, in accordance with one embodiment of the invention.

FIG. 3A is an enlarged cross sectional view of a resiliently-biased sensing mechanism of the cable track monitoring system of FIG. 3 encased within line 3A-3A thereof; and FIGS. 4 and 5 are cross sectional side views of an alternative resiliently-biased sensing mechanism for use with a cable track monitoring system, shown during normal and faulty operation, respectively, in accordance with another embodiment of the invention.

DETAILED DESCRIPTION OF THE EXEMPLARY EMBODIMENTS

The systems and methods described herein provide, in accordance with different examples, a cable track monitoring system and method. For instance, in some aspects, the below described systems and methods permit for the automated, and in some embodiments, real-time monitoring of a cable track in operation so as to detect any potential, predictable and/or current structural wear and/or failures that may have an undesirable impact on the safe, reliable and/or continuous operation of the system serviced by this cable track.

As will be appreciated by the skilled artisan, while the below examples are cast within the context of an industrial assembly line, such as in the automotive industry, the systems and methods considered herein are not so limited and may rather be applied within different contexts where cable tracks are used, such as in industrial or material processing, transportation, oil and gas, and the like. Further, the skilled artisan will appreciate that the term "cable track" is used generically herein to define a means by which cables, wires, tubing and/or other such conduits used to feed, power and/or otherwise operate mobile devices or machinery can be managed and guided along a designated path, and that other such means as may also be known by other names, such as cable carriers, may equally be considered herein to benefit from the features and aspects of the monitoring systems and methods described herein. Likewise, while the following examples will refer mostly to the use of cable tracks in the management of cables, generically, it will be appreciated that these cable tracks may also be used in the management of electrical wires, tubing, fluid conduits (e.g. fluid inlets/outlets, pneumatic conduits, etc.) and the like without departing from the general scope and nature of the present disclosure.

These and other applications will be described in greater detail below, in a non-restrictive manner, with reference to the below description of exemplary embodiments.

With reference now to FIG. 1, and in accordance with one embodiment, a cable track monitoring system, generally referred to using the numeral 100, will now be described. The system 100 is generally provided for monitoring operation of a cable track 102 operatively mounted between an anchoring unit 104 and a mobile unit 106 in designating a deployable cabling path therebetween as the mobile unit 106 travels relative to the anchoring unit 104 (e.g. along displacement arrow A). In this example, the mobile unit 106 travels linearly in a substantially horizontal reciprocating motion, entraining the cable track 102, and the various cables, wires and/or conduits 108 disposed therealong, to furl and unfurl as the mobile unit 106 travels. A cable track tray 110 is also provided to progressively house a lower portion of the cable track 102 as it unfurls, this lower portion of the cable track 102 being progressively rolled out of the tray 110 as it furls back up.

The monitoring system 100 comprises a monitoring cable 112 that runs within the cable track 102 along the cabling path, namely along with the other cables, wires and/or conduits 108 housed within the cable track 102. Accordingly, as the cable track 102 furls and unfurls as the mobile unit 106 travels relative to the anchoring unit 104 to define the deployable cabling path, the monitoring cable 112 run along the cable track 102 will equally furl and unfurl as the mobile unit 106 travels. In one embodiment, the monitoring cable 112 is run along the cable track 102 within a protective tubing 114, such as a corrugated compressible protective tubing consisting of a low friction material (better seen in FIG. 2), thus reducing the possibility of wear of, or other such undesirable issues with the monitoring cable 112 during operation of the cable track 102. The use of a low friction, corrugated and compressible protective tubing 114 in this embodiment serves to transfer dimensional changes in the cable track length to the monitoring cable efficiently.

The system further comprises a sensor 115 fixedly mounted, in this embodiment, to the anchoring unit 104, and operatively coupled to the monitoring cable 112 to sense a tension variation therein as the mobile unit 106 travels relative to the anchoring unit 104. To do so, the monitoring cable 112, in this embodiment, is operatively coupled to the anchoring unit 104 via the sensor 115, whereas the opposite end of the cable 112 is fixedly coupled to the mobile unit 106. Accordingly, tension variations in the cable 112 are directly exerted to the sensor 115 to be monitored thereby. Alternatively, the sensor may rather be fixedly coupled to the mobile unit 106, with the monitoring cable 112 operatively coupled thereto and oppositely fixedly coupled to the anchoring unit 104 to provide a similar effect.

In one embodiment a tension variation monitored by the sensor 115 is used to observe unusual variations that may be associated with a cable track malfunction, such as wear, structural weakening, component breakage, and/or component/system failure, to name a few examples. Tension variations may be monitored in real-time by an operator, stored in a computer-readable memory or otherwise tracked via a printed recording or the like, or again tracked automatically via a processing unit (e.g. via unit 116 of FIG. 1) to raise an alert (e.g. via an audible or visual alarm, indicia or cue, or again via a networked industrial management/operation system) upon tracked variations exceeding a designated threshold, for example. In some embodiments, the system may be configured to automatically stop operation of the equipment operating the cable track 102 (i.e. stop a displacement of the mobile unit 106) where an imminent or actual failure is detected and/or predicted from the monitored tension variations. In these or other embodiments, different alerts may be implemented, for example, based on a perceived severity (e.g. amplitude and/or frequency of observed tension variations), in some examples escalating an alert as observed tension variations increase in amplitude and/or frequency (e.g. indicative of an increasingly probable failure and/or increasingly suboptimal operational state).

In this particular embodiment, the sensor is coupled to a processing unit 116, such as a dedicated, multipurpose and/or networked computing device, to receive and process sensor data and, in some embodiments, raise an appropriate alert upon this data satisfying one or more designated criteria indicative of a current or foreseeable cable track malfunction, for example. In this embodiment, the processing unit 116 comprises one or more input/output interfaces 118 to receive monitoring signals from the sensor 115 and optionally convey operational parameters thereto, as appropriate; a memory 120 (e.g. one or more fixed or removable computer-readable media or drives) to store and track sensed system variations; one or more processors 122 for processing the acquired sensor data and, in one embodiment, communicating or raising a designated alert; and a local or networked user/network interface 124, such as a graphical user interface (GUI) or the like to provide user access to the system, acquired data and alerts, as appropriate given the application and context at hand.

As will be appreciated by the skilled artisan, the processing unit 116 may take various forms without departing from the general scope and nature of the present disclosure. For instance, a small scale operation may benefit from a dedicated processing unit operated locally and associated with an immediately accessible alerting system, whereby immediate attention may be brought to the monitored cable track upon an alert being raised. In a larger scale operation, for example where multiple cable tracks are monitored simultaneously, the processing unit 116 may consist of a networked monitoring application, for example integrated or implemented within a larger industrial management program or system to relay local alerts through a global management system in directing appropriate staff or personnel, as needed, to attend to defective cable tracks identified by the system. A globally integrated application may be further amenable to invoking a local system shut-down in the event that a current or imminent cable track failure is detected. These and other such variations will be readily apparent to the skilled artisan, and are therefore intended to fall within the general scope and nature of the present disclosure.

With added reference to FIGS. 2 and 2A, and in accordance with one embodiment, the sensor 115 comprises a resiliently-biased sensing mechanism coupleable at one end of the monitoring cable 112 such that observable tension variations in the cable 112 induce an observable displacement of the sensing mechanism. In this particular example, the monitoring cable 112 is fixedly coupled to a lever-activated limit switch 128, whereby the cable 112 is fixedly coupled toward the end of the switch's activation lever 130 to bias this lever toward the cable track 102 and act against an oppositely directed spring 132 effectively coupled between the lever 130 and anchoring unit 104. In normal operation, and as best seen in FIG. 2A, the limit switch 128 is set so to have the lever 130 equally biased by cable 112 and spring 132, namely to have the lever 130 extend substantially at right angle to the cable 112 and thus equally monitor increases and decreases in cable tension. Accordingly, bidirectional tension variations may be monitored by the limit switch 128, and a signal representative thereof (e.g. a discrete or continuous signal) generated for monitoring.

With reference now to FIGS. 3 and 3A, upon failure of the cable track 102, in this example represented by a complete structural failure 134 resulting in the partial collapse of the cable track 102, a tension in the monitoring cable 112 will be reduced (i.e. released by the failure-induced shortening of the cabling path in this example), thus resulting in an observable and recordable displacement of the limit switch's spring-biased lever 130. As will be appreciated by the skilled artisan, other cable track failures may result in an increased tension in the monitoring cable 112, equally observable by the herein-described sensing mechanism. In the event of such a system failure, the monitoring system 100 may be configured to raise an alarm, and in some embodiments, provoke a system shutdown to avoid further damage to the cable track 112, the cables 108 run therealong, and/or equipment associated with the mobile unit 106, for example.

While such complete or partial cable track failures may be more importantly monitored by the herein-described embodiment, the system 100 may also be used to detect smaller or less drastic failures, and/or again detect signs of unusual or accumulated wear, imminent or predictable failure, and other maintenance concerns of interest. For example, where one or more components of the cable track begin to show signs of unusual or accumulated wear, the cable track 102 may begin to show signs of increased sagging, particularly in the upper run of the cable track during operation. Such increased sagging may be detected by the herein-described system through an observable tension increase in the monitoring cable 112 (i.e. the effective length of the cable track 102 will increase relative to that of the cable 112, thus invoking a corresponding displacement of the lever 130). Detection of undue sag or wear may thus result in early maintenance or replacement of the cable track 102, or component thereof, and avoidance of unnecessary and potentially costly breakdowns.

In one embodiment, cable track sag may be geometrically modeled to compute a corresponding increase in length, and thus a resulting deviation in monitoring cable tension. For example, the sag may be modeled as defining a downward arc relative to, in this example, a horizontal line, whereby a relative increase in cable track length may be characterized by an increased depth and width of this arc. This geometric modeling may thus be associated with different degrees of wear, and accordingly, to different sensor settings by which to generate an alert upon the cable track manifesting signs of undue or excessive wear before an actual failure occurs.

In other situations, the monitoring system 100 may allow for the general monitoring of wear in the cable track's various components (e.g. joints, modules, etc.), whereby faulty or worn components may induce unusual perturbations to the otherwise predictable furling and unfurling cabling path. For example, a worn joint or module may cause the cable track to jump or buckle in operation, which may trigger a corresponding variation in cable tension and thus trigger recordal of an undesirable event by the monitoring system. Where the triggered event is not repeated, or of a magnitude previously designated as "normal" or as being of likely limited consequence, the event may be ignored by the system (though still possibly recorded for future consideration). However, where the triggered event is repeated, for example every cycle of the cable track's operation, or again where a magnitude of the event is above a designated threshold, the system may raise an alert and invoke a maintenance check to prevent further wear and/or a predictable or imminent failure. Accordingly, by adjusting a sensitivity of the sensor 115, and associated monitoring software/application, the monitoring system 100 may be configured to discriminate or differentiate between regular or random operational jitters and vibrations, and potentially problematic structural variations in cable track operation.

As will be appreciated by the skilled artisan, different sensor mechanisms may also be considered within the present context without departing from the general scope and nature of the present disclosure. For example, and with particular reference to FIGS. 4 and 5, an alternative sensing mechanism may comprise a pneumatically-biased slide sensor 228 configured and operated much like the spring-biased lever-activated limit switch 128 of FIGS. 3 and 3A. In this example, a monitoring cable 212 is fixedly coupled to an external end of a biased slide member 230 of the sensor 228, whereas an opposed and internal end (not shown) of this slide member 230 is internally monitored, for example via a proximity sensor (not shown), such that a displacement of this slide member 230 under action from tension variations in the monitoring cable 212 can be translated into a monitoring signal, again, much like as described above. For example, the sensor 228 may be observed to rest substantially around a first extended position, as seen in FIG. 4, during normal operation, and move to a shortened position, as seen in FIG. 5, during a malfunction or upon the cable track furling or unfurling through a problematic position.

As will be appreciated by the skilled artisan, other sensing mechanisms may also be applied in the present context without departing from the general scope and nature of the present disclosure.

While the present disclosure describes various exemplary embodiments, the disclosure is not so limited. To the contrary, the disclosure is intended to cover various modifications and equivalent arrangements included within the general scope of the present disclosure.

What is claimed is:

1. A monitoring system for a cable track operatively mounted between an anchoring unit and a mobile unit in designating a deployable cabling path therebetween as the mobile unit travels relative to the anchoring unit, the system comprising:

a monitoring cable to be run within the cable track along the cabling path; and a sensor fixedly mountable relative to one of the anchoring unit and the mobile unit and operatively coupleable to said monitoring cable to sense an undesirable tension variation therein as the mobile unit travels relative to the anchoring unit;

wherein said sensor is operable to produce an output indicative of said undesirable tension variation as representative of suboptimal operation of the cable track.

2. The monitoring system of claim 1, wherein said sensor is operable to issue an alert upon said undesirable tension variation exceeding a designated threshold.

3. The monitoring system of claim 1, wherein the cable track furls and unfurls as the mobile unit travels relative to the anchoring unit thus defining the deployable cabling path, and wherein the monitoring cable is run within the cable track to furl and unfurl accordingly.

4. The monitoring system of claim 1, wherein said monitoring cable is operatively coupled to said sensor at said one of the anchoring unit and the mobile unit, and fixedly coupled to the other one of said anchoring unit and the mobile unit.

5. The monitoring system of claim 4, wherein said sensor is fixedly coupled to said anchoring unit and wherein said monitoring cable is fixedly coupled to said mobile unit.

6. The monitoring system of claim 1, wherein said sensor comprises a resiliently-biased sensing mechanism coupleable to said monitoring cable such that said tension variation induces an observable displacement of said sensing mechanism, said sensor operable to continuously monitor said observable displacement during operation of the cable track.

7. The monitoring system of claim 6, wherein said sensor is operable to issue an alert upon said observable displacement exceeding a preset displacement threshold.

8. The monitoring system of claim 6, wherein said resiliently-biased mechanism comprises a spring-biased lever-activated switch.

9. The monitoring system of claim 6, wherein said resiliently-biased mechanism comprises a pneumatically-biased slide-activated switch.

10. The monitoring system of claim 1, further comprising a protective tube to house said monitoring cable within the cable track along the cabling path.

11. The monitoring system of claim 10, wherein said protective tube is a low friction, corrugated protective tube.

12. The monitoring system of claim 1, further comprising a processing unit for monitoring a frequency of said output, and for outputting an alert as a function of said frequency.

13. The monitoring system of claim 12, wherein said alert is output upon said frequency exceeding a designated frequency threshold.

14. The monitoring system of claim 1, further comprising a processing unit for monitoring an amplitude of said undesirable tension variation via said output, and for outputting an alert as a function of said amplitude.

15. A method for monitoring a cable track operatively mounted between an anchoring unit and a mobile unit in designating a deployable cabling path as the mobile unit moves relative to the anchoring unit, the method comprising:
 running a monitoring cable along the cable track;
 monitoring tension variations in said monitoring cable as the mobile unit moves relative to the anchoring unit; and
 automatically producing an output signal representative of said monitored tension variations as indicative of a cable track operation.

16. The method of claim 15, wherein said monitoring step comprises continuously monitoring said tension variations in real-time.

17. The method of claim 15, further comprising the step of raising an alert upon said monitored tension variations exceeding a designated threshold.

18. The method of claim 17, wherein said designated threshold comprises at least one of a tension variation amplitude threshold and a tension variation frequency threshold.

19. The method of claim 15, further comprising fixedly coupling a tension-sensitive sensor relative to one of said anchoring unit and said mobile unit, wherein said running step comprises operatively coupling a first end of said monitoring cable to said tension-sensitive sensor and fixedly coupling the other end of said monitoring cable relative to the other one of said anchoring unit and said mobile unit, and wherein said monitoring step comprises monitoring said tension variations via said tension-sensitive sensor.

20. The method of claim 15, wherein said running step comprises running a protective tube along the cable track and running said monitoring cable within said protective tube.

21. The method of claim 15, wherein said running step comprises running said monitoring cable within the cable track along with other cables operatively disposed therealong to operate the mobile unit.

* * * * *